(12) United States Patent
Vijithakumara

(10) Patent No.: US 11,006,859 B2
(45) Date of Patent: May 18, 2021

(54) METHODS AND SYSTEMS FOR DISABLING A STEP-COUNTING FUNCTION OF A WEARABLE FITNESS TRACKER WITHIN A VEHICLE

(71) Applicant: Toyota Motor North America, Inc., Plano, TX (US)

(72) Inventor: Evan Vijithakumara, Frisco, TX (US)

(73) Assignee: TOYOTA MOTOR NORTH AMERICA, INC., Plano, TX (US)

( * ) Notice: Subject to any disclaimer, the term of this patent is extended or adjusted under 35 U.S.C. 154(b) by 0 days.

(21) Appl. No.: 16/528,969

(22) Filed: Aug. 1, 2019

(65) Prior Publication Data

US 2021/0030310 A1 Feb. 4, 2021

(51) Int. Cl.
*G08B 21/00* (2006.01)
*A61B 5/11* (2006.01)
*A61B 5/00* (2006.01)
*A61B 5/18* (2006.01)
*A61B 5/024* (2006.01)

(52) U.S. Cl.
CPC ............ *A61B 5/1118* (2013.01); *A61B 5/681* (2013.01); *A61B 5/02438* (2013.01); *A61B 5/1123* (2013.01); *A61B 5/18* (2013.01); *A61B 5/7264* (2013.01); *A61B 2562/0219* (2013.01)

(58) Field of Classification Search
CPC ...... A61G 2203/12; A61G 7/018; A61G 7/05; A61G 7/0506; A61G 12/00; A61G 2203/46; A61G 2203/70; A61G 2205/60; A61G 7/015; A61G 7/0507; A61G 7/0514; A61B 5/1118; A61B 5/681; A61B 5/18; A61B 5/02438; A61B 2562/0219; A61B 5/1123; A61B 5/7264
USPC .......................................... 340/4.34
See application file for complete search history.

(56) References Cited

U.S. PATENT DOCUMENTS

| | | | | |
|---|---|---|---|---|
| 5,808,159 A * | 9/1998 | Giebeler | ............... | C07C 209/86 564/497 |
| 8,761,821 B2 * | 6/2014 | Tibbitts | ................. | H04W 48/04 455/517 |
| 9,037,125 B1 * | 5/2015 | Kadous | ............. | H04M 1/72577 455/418 |
| 9,204,258 B2 | 12/2015 | Chen et al. | | |
| 9,294,603 B2 * | 3/2016 | Fischer | .................... | G07C 9/29 |
| 9,386,447 B2 * | 7/2016 | Tibbitts | .................. | H04W 4/48 |
| 9,413,871 B2 | 8/2016 | Nixon et al. | | |
| 9,924,027 B2 * | 3/2018 | Rajendran | ......... | H04M 1/72577 |

(Continued)

FOREIGN PATENT DOCUMENTS

| CN | 105606120 A | 5/2016 |
|---|---|---|
| CN | 106289306 A | 1/2017 |

*Primary Examiner* — Mark S Rushing
(74) *Attorney, Agent, or Firm* — Dinsmore & Shohl LLP

(57) ABSTRACT

A method for disabling a step-counting function of a wearable fitness tracker includes detecting a vehicle start-up event of a vehicle with one or more vehicle sensors, and sending an in-vehicle confirmation signal from one or more vehicle communication modules to one or more wearable fitness trackers positioned within the vehicle in response to detecting the vehicle start-up event. The in-vehicle confirmation signal is configured to be received by the one or more wearable fitness trackers and cause the one or more wearable fitness trackers to automatically disable the step-counting function of the one or more wearable fitness trackers.

8 Claims, 3 Drawing Sheets

(56) References Cited

U.S. PATENT DOCUMENTS

| | | | |
|---|---|---|---|
| 10,572,123 B2* | 2/2020 | Penilla | B60W 40/08 |
| 2004/0140348 A1 | 7/2004 | Fromm | |
| 2006/0020177 A1* | 1/2006 | Seo | A61B 5/222 |
| | | | 600/300 |
| 2012/0172012 A1* | 7/2012 | Sumcad | H04W 4/12 |
| | | | 455/414.1 |
| 2012/0288126 A1* | 11/2012 | Karkkainen | G10L 25/78 |
| | | | 381/309 |
| 2012/0330608 A1* | 12/2012 | Wang | G01C 22/006 |
| | | | 702/160 |
| 2013/0179110 A1 | 7/2013 | Lee | |
| 2016/0007888 A1 | 1/2016 | Nieminen et al. | |
| 2016/0183869 A1* | 6/2016 | Oh | A61B 5/486 |
| | | | 600/595 |
| 2017/0082649 A1* | 3/2017 | Tu | G01P 13/00 |
| 2017/0353597 A1* | 12/2017 | Wolterman | H04M 1/72577 |
| 2018/0132762 A1* | 5/2018 | Kashiwagi | A61B 5/1118 |
| 2018/0370360 A1* | 12/2018 | Hannon | B60K 35/00 |

* cited by examiner

METHODS AND SYSTEMS FOR DISABLING A STEP-COUNTING FUNCTION OF A WEARABLE FITNESS TRACKER WITHIN A VEHICLE

TECHNICAL FIELD

The present specification generally relates to disabling functions on a wearable fitness tracker and, more specifically, to methods and systems for disabling a step-counting function of a wearable fitness tracker within a vehicle.

BACKGROUND

Fitness trackers may be equipped with algorithms that may infer whether or not a user wearing the fitness tracker is in a vehicle. However, because such fitness trackers are not directly paired with the vehicle, there is no guarantee that such inferences are correct.

Accordingly, a need exists for alternative methods and systems for disabling a step-counting function of a wearable fitness tracker when within a vehicle.

SUMMARY

In one embodiment, a method for disabling a step-counting function of a wearable fitness tracker includes detecting a vehicle start-up event of a vehicle with one or more vehicle sensors, and sending an in-vehicle confirmation signal from one or more vehicle communication modules to one or more wearable fitness trackers positioned within the vehicle in response to detecting the vehicle start-up event. The in-vehicle confirmation signal is configured to be received by the one or more wearable fitness trackers and cause the one or more wearable fitness trackers to automatically disable the step-counting function of the one or more wearable fitness trackers.

In another embodiment, a system for disabling a step-counting function of a wearable fitness tracker includes one or more processors, one or more vehicle sensors configured to output a vehicle start-up signal indicative of a vehicle start-up event of a vehicle, one or more vehicle communication modules communicatively coupled to the one or more processors and configured to output an in-vehicle confirmation signal, and one or more memory modules communicatively coupled to the one or more processors. The one or more memory modules store logic that, when executed by the one or more processors, causes the system to detect the vehicle start-up event based on the vehicle start-up signal from the one or more vehicle sensors, and send the in-vehicle confirmation signal from the one or more vehicle communication modules to one or more wearable fitness trackers positioned within the vehicle in response to detecting the vehicle start-up event. The in-vehicle confirmation signal is configured to disable the step-counting function of one or more wearable fitness trackers in response to receiving the in-vehicle confirmation signal from the one or more vehicle communication modules.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

The figures generally depict systems and methods for disabling a step-counting function of a wearable fitness tracker while the wearable fitness tracker is positioned within a vehicle. Systems according to the present disclosure generally include one or more processors, one or more vehicle sensors, one or more vehicle communication modules, and one or more memory modules. As will be described in greater detail below, the systems as disclosed herein can detect a vehicle start-up event based on a vehicle start-up signal from the one or more vehicle sensors and send an in-vehicle confirmation signal from the one or more vehicle communication modules to the one or more wearable fitness trackers positioned within the vehicle in response to detecting the vehicle start-up event. The in-vehicle confirmation signal is configured to be received by the one or more wearable fitness trackers and cause the one or more wearable fitness trackers to automatically disable the step-counting function of the one or more wearable fitness trackers. Accordingly, false step counts that may occur when a user of a wearable fitness tracker is positioned within a vehicle (and not walking) may be avoided. Additionally, such systems would be able to communicate with the one or more wearable fitness trackers without needing to directly pair or connect the one or more wearable fitness trackers to the system or to the vehicle. Various embodiments of the systems and methods for disabling a step-counting function of a wearable fitness tracker will be described in more detail herein.

Figure 1:
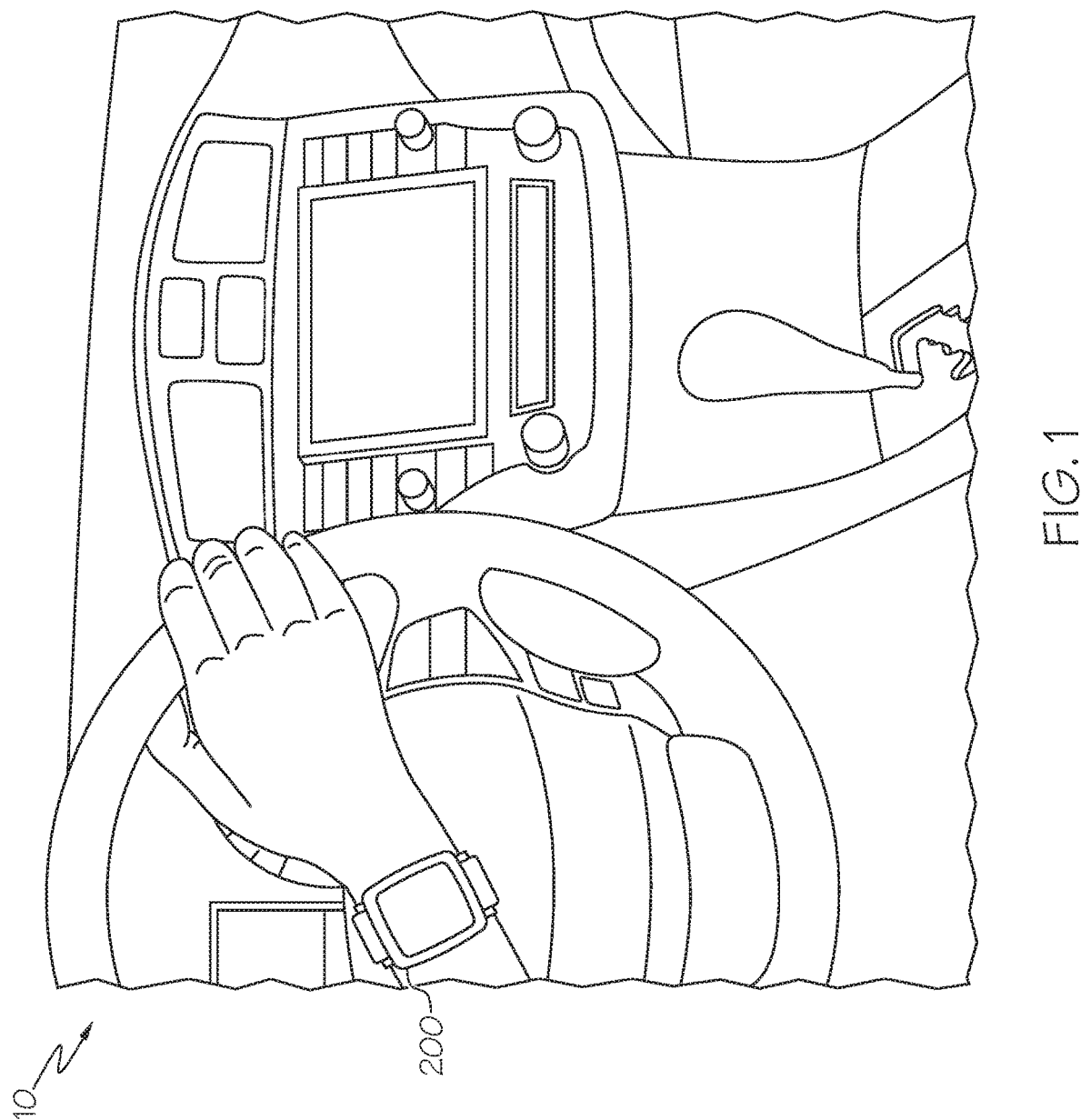
FIG. 1 illustrates a fitness tracker positioned within a vehicle, according to one or more embodiments shown and described herein.

FIG. 1 generally illustrates a wearable fitness tracker 200 within an interior of a vehicle 10. As used herein, the term "wearable fitness tracker" may include any device that is configured to count the steps of a user. Accordingly, a wearable fitness tracker may include a pedometer-type device. Wearable fitness trackers may include watches, wristbands, clips, necklaces, shoe accessories, devices that are stowed within the clothing of the user, etc. Wearable fitness trackers according to the present disclosure may include a processor, memory module, and receiver modules (e.g., microphones, Bluetooth Receiver Modules, radio frequency receiver modules, cellular signal receiver modules, WiFi signal receiver modules, nearfield communication receiver modules, etc.). As will be described in greater detail herein, the wearable fitness tracker may receive signal from the vehicle 10, or a system within the vehicle, and based on the signal deactivate one or more functions of the wearable fitness tracker. In particular, the present disclosure focuses on the deactivation of a step-counting function of the wearable fitness tracker 200. However, other functions are contemplated and possible (e.g., heart monitoring functions, calorie burn estimation functions, etc.).

Additionally, it is noted that while vehicle 10 is illustrated as a car, the vehicle 10 may include any type of passenger vehicle including, land vehicles (e.g., cars, vans, trucks, busses, trains, etc.), aquatic vehicles (e.g., boats, submarines, etc.), or air vehicles (e.g., airplanes, helicopters, etc.).

Figure 2:
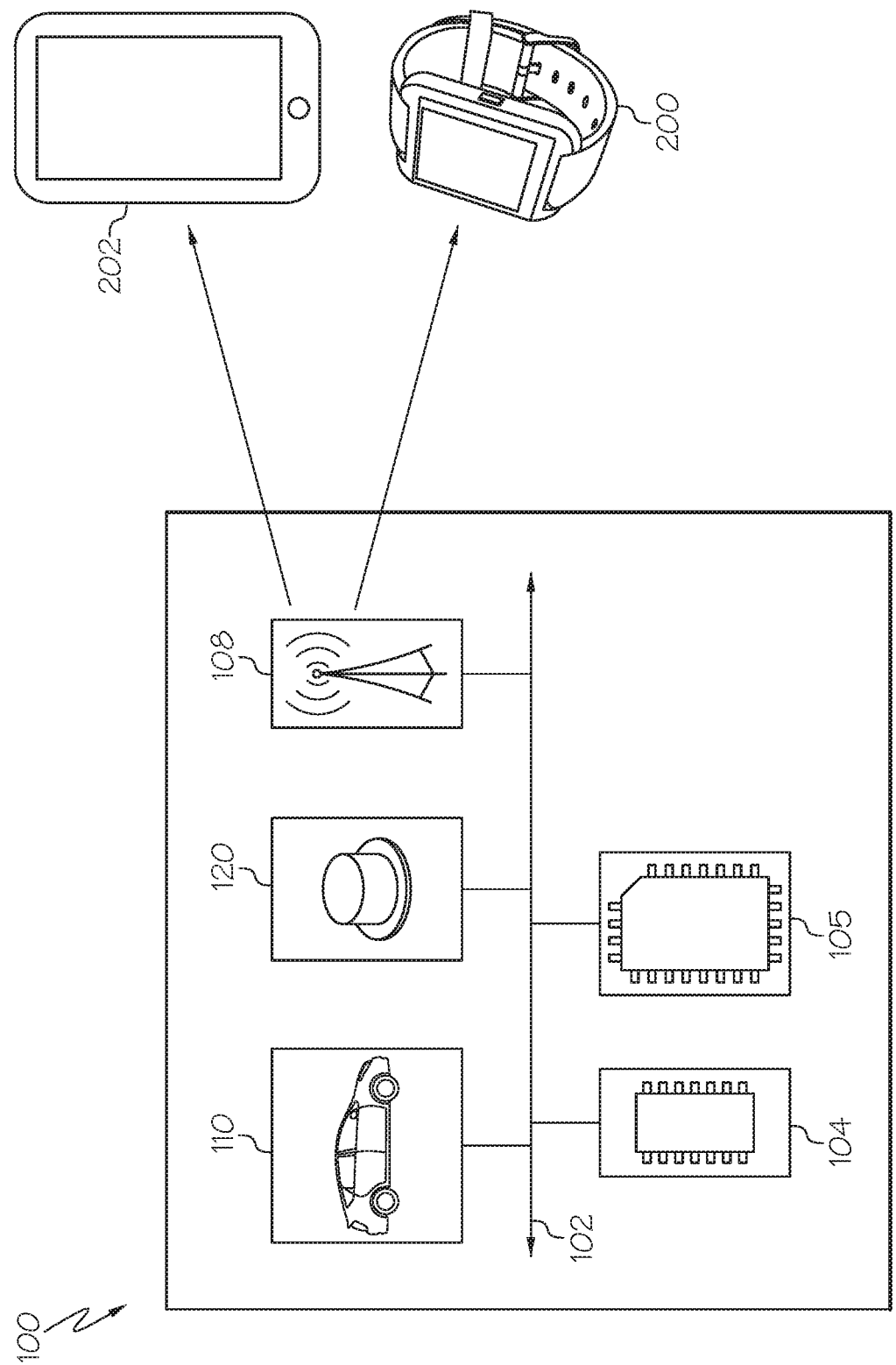
FIG. 2 schematically illustrates a system for disabling a step-counting function of a wearable fitness tracker, according to one or more embodiments shown and described herein.

Referring now to FIG. 2, a system 100 for disabling a step-counting function of a wearable fitness tracker is schematically illustrated. The system 100 may be directly incorporated into vehicle systems or separate therefrom. The system 100 may generally include a communication path 102, one or more processors 104, one or more memory modules 105, one or more vehicle sensors 110, one or more vehicle communication modules 108, and one or more user input devices 120. It is noted that systems described herein may include a greater or fewer number of modules without departing from the scope of the present disclosure.

The communication path 102 provides data interconnectivity between various modules of the system 100. Specifically, each of the modules can operate as a node that may send and/or receive data. In some embodiments, the communication path 102 includes a conductive material that permits the transmission of electrical data signals to processors, memories, sensors, and actuators throughout the system 100. In another embodiment, the communication path 102 can be a bus, such as for example a LIN bus, a CAN bus, a VAN bus, and the like. In further embodiments, the communication path 102 may be wireless and/or an optical waveguide. Components that are communicatively coupled may include components capable of exchanging data signals with one another such as, for example, electrical signals via conductive medium, electromagnetic signals via air, optical signals via optical waveguides, and the like.

The one or more processors 104 are communicatively coupled with the one or more memory modules 105 over the communication path 102. The one or more processors 104 may include any device capable of executing machine-readable instructions stored on a non-transitory computer-readable medium. The one or more processors 104 may include a controller, an integrated circuit, a microchip, a computer, and/or any other computing device.

The one or more memory modules 105 are communicatively coupled to the one or more processors 104 over the communication path 102. The one or more memory modules 105 may be configured as volatile and/or nonvolatile memory and, as such, may include random access memory (including SRAM, DRAM, and/or other types of RAM), flash memory, secure digital (SD) memory, registers, compact discs (CD), digital versatile discs (DVD), and/or other types of non-transitory computer-readable mediums. Depending on the particular embodiment, these non-transitory computer-readable mediums may reside within the system 100 and/or external to the system 100. The embodiments described herein may utilize a distributed computing arrangement to perform any portion of the logic described herein. The one or more memory modules 105 may be configured to store one or more pieces of logic to allow the system 100 to communicate with one or more wearable fitness trackers 200 to disable a step-counting function of the one or more wearable fitness trackers, as described in more detail below.

Embodiments of the present disclosure include logic stored on the one or more memory modules 105 that include machine-readable instructions and/or an algorithm written in any programming language of any generation (e.g., 1GL, 2GL, 3GL, 4GL, and/or 5GL) such as, machine language that may be directly executed by the one or more processors 104, assembly language, object-oriented programming (OOP), scripting languages, microcode, etc., that may be compiled or assembled into machine readable instructions and stored on a machine readable medium. Similarly, the logic and/or algorithm may be written in a hardware description language (HDL), such as logic implemented via either a field-programmable gate array (FPGA) configuration or an application-specific integrated circuit (ASIC), and their equivalents. Accordingly, the logic may be implemented in any conventional computer programming language, as pre-programmed hardware elements, and/or as a combination of hardware and software components. As will be described in greater detail herein, logic executed by the one or more processors 104 allows the system 100 to detect a vehicle start-up event and send an in-vehicle confirmation signal to the one or more fitness trackers within the vehicle 10 to cause the fitness tracker to disable it step-counting function.

The one or more vehicle sensors 110 may be communicatively coupled to the one or more processors 104 of the communication path 102. The one or more vehicle sensors 110 may be any sensor configured to output one or more signals indicative of a status of a vehicle 10. For example, the one or more signals may include a vehicle start-up signal and/or a vehicle-exiting signal.

For outputting a vehicle start-up signal, the one or more vehicle sensors 110 may include door sensors, ignition sensors, gear shift sensors, seat belt sensors, seat sensors (e.g., pressure sensors), or any sensor which may provide feedback to the one or more processors 104 of a vehicle start-up event or intention for a vehicle start-up event to occur. For example, a door sensor may output a signal indicative of a vehicle door being opened and or closed. Based on the signal from the door sensor, the one or more processors 104 may execute logic to cause the system 100 to determine that a user is entering the vehicle 10. A user entering the vehicle 10 may be considered a vehicle start-up event. As another example, an ignition sensor may output a signal indicative a key being inserted into the ignition or the ignition being otherwise activated (e.g., through twisting of the key, pushing a button, etc.) which may also considered a vehicle start-up event.

For outputting a vehicle-exiting signal, the one or more vehicle sensors 110 may include door sensors, ignition sensors, gear shift sensors, seat belt sensors, seat sensors (e.g., pressure sensors), or any sensor which may provide feedback to the one or more processors 104 of a vehicle exiting event or intention for a vehicle exiting event to occur. The one or more vehicle sensors 110 for outputting a vehicle-exiting signal may be the same or different from the one or more vehicle sensors 110 for outputting a vehicle start-up signal. In embodiments, a door sensor may output a signal indicative of a vehicle door being opened and or closed. Based on the signal from the door sensor, the one or more processors 104 may execute logic to cause the system 100 to determine that a user is exiting the vehicle 10. A user exiting the vehicle 10 may be considered a vehicle-exiting event. As another example, an ignition sensor may output a signal indicative a key being withdrawn from the ignition or the ignition being otherwise deactivated (e.g., through twisting of the key, pushing a button, etc.) which may also considered a vehicle-exiting event.

In various embodiments, multiple vehicle sensors 110 may be used, and based on the various sensor outputs, the one or more processors 104 may execute logic to allow the system 100 to determine that a vehicle start-up event or a vehicle-exiting event is occurring. For example, where a door sensor outputs a signal of a door opening/closing and a seat sensor outputs a signal of a weight being supported on a seat, the one or more processors 104 may execute logic to allow the system 100 to determine that a vehicle start-up event is occurring. Similarly, wherein a door sensor output a signal of a door opening/closing and a seat sensor output a signal of no or negligible weight being supported on the seat, the one or more processors 104 may execute logic to allow the system 100 to determine a vehicle-exiting event is occurring. Other combination of sensors are contemplated and possible without departing from the scope of the present disclosure.

The one or more vehicle communication modules 108 may be communicatively coupled to the one or more processors 104 over the communication path 102. The one or more vehicle communication modules 108 may include any device configured to output a beacon or signal which is receivable by the one or more wearable fitness trackers 200. For example, the one or more vehicle communication modules 108 can be any device capable of transmitting and/or receiving a signal to and/or from one or more wearable fitness trackers 200 and/or one or more mobile devices 202 (e.g., smart phone, tablet, laptop, etc.). Accordingly, the one or more vehicle communication modules 108 can include a transmitter for sending a beacon or a signal to the wearable tracker device and/or a mobile device. In some embodiments, the one or more vehicle communication modules 108 may be a communication transceiver for sending and/or receiving any wired or wireless communication. For example, the one or more vehicle communication modules 108 may include an antenna, a modem, LAN port, Wi-Fi card, WiMax card, mobile communications hardware, radio frequency communication hardware, near-field communication hardware, satellite communication hardware, and/or any wired or wireless hardware for communicating with wearable fitness tracker(s) and/or mobile devices.

The one or more vehicle communication modules 108 may include hardware configured to operate in accordance with the Bluetooth wireless communication protocol. In another embodiment, one or more vehicle communication modules 108 may include a Bluetooth send and/or receive module for sending and/or receiving Bluetooth communications to/from a wearable fitness tracker and/or a mobile device. The one or more wearable fitness trackers 200 and/or a one or more mobile devices 202 may be configured to detect the Bluetooth signal. Upon detection of the Bluetooth signal, the one or more wearable fitness trackers 200 may determine that the one or more wearable fitness trackers 200 are within the vehicle 10, as illustrated in FIG. 1, and disable the step-tracking function of the one or more wearable fitness trackers 200.

In some embodiments, the one or more vehicle communication modules 108 may include a sound transmitter that is configured to transmit an audio tone undetectable by human ears (e.g., a sound outside of the range of about 20 HZ to about 20 kHz. For example, the sound transmitter may transmit of high frequency tone of greater than 20 kHz. The wearable fitness tracker and/or a mobile device may be configured with a listening device that is able to detect the high frequency tone. Upon detection of the high frequency tone, the one or more wearable fitness trackers 200 may determine that the one or more wearable fitness trackers 200 are within the vehicle 10 and disable the step-tracking function of the one or more wearable fitness trackers 200.

In embodiments, upon detection of a vehicle start-up event, the system 100 may automatically send the in-vehicle confirmation signal with the one or more vehicle communication modules 108 to the one or more wearable fitness trackers 200 positioned within the vehicle 10. In some embodiments, the in-vehicle confirmation signal may be transmitted for a first time period (e.g., 5 seconds or more, 30 seconds or more, 60 second or more, etc.) upon detecting the vehicle start-up event. In some embodiments, the one or more vehicle communication modules 108 may be a transceiver that is able to receive requests from the one or more wearable fitness trackers and/or a mobile device, requesting that the system output the in-vehicle confirmation signal. For example, when a mobile device pairs to the system through Bluetooth, such pairing may prompt the one or more mobile devices 202 to request the system 100 output the in-vehicle communication signal to be received by the one or more wearable fitness trackers 200 and/or the one or more mobile devices.

Additionally, upon detection of a vehicle-exiting event with the one or more vehicle sensors 110, the one or more vehicle communication modules 108 can output an out-of-vehicle confirmation signal from the one or more vehicle communication modules 108 to the one or more wearable fitness trackers 200 in response to detecting the vehicle-exiting event. In some embodiments, the out-vehicle confirmation signal may be transmitted for a second time period (e.g., 5 seconds or more, 30 seconds or more, 60 second or more, etc.) upon detecting the vehicle-exiting event. The out of vehicle confirmation signal may be the same or a different signal from the out of in-vehicle confirmation signal. For example, the out of vehicle confirmation signal may have the same or different tone, frequency, etc. as the in-vehicle confirmation signal.

In embodiments, wherein the mobile device and/or the wearable fitness tracker, in response to receiving the in-vehicle confirmation signal and/or out-of-vehicle confirmation signal may output a prompt requesting that the user confirm that the wearable fitness tracker and/or the mobile device is positioned within the vehicle. In some embodiments, only the mobile device may receive the signal and then control the wearable fitness tracker to stop the step-counting function.

It is noted that while the present application focuses on the step-counting functionality of the wearable fitness tracker, other functions may also be disrupted when the in-vehicle confirmation signal is received. For example, a heart monitoring function and/or a calorie burn estimation function.

In embodiments, the vehicle, the mobile device, or the wearable fitness tracker may include user input devices 120 (e.g., touchscreens, buttons, etc.) to override the system so as to not turn-off the step-counting function. For example, a user of a wearable fitness device 200 may not desire to stop the step-counting function when riding on a vehicle wherein the user is standing (e.g., on a bus or train).

Figure 3:
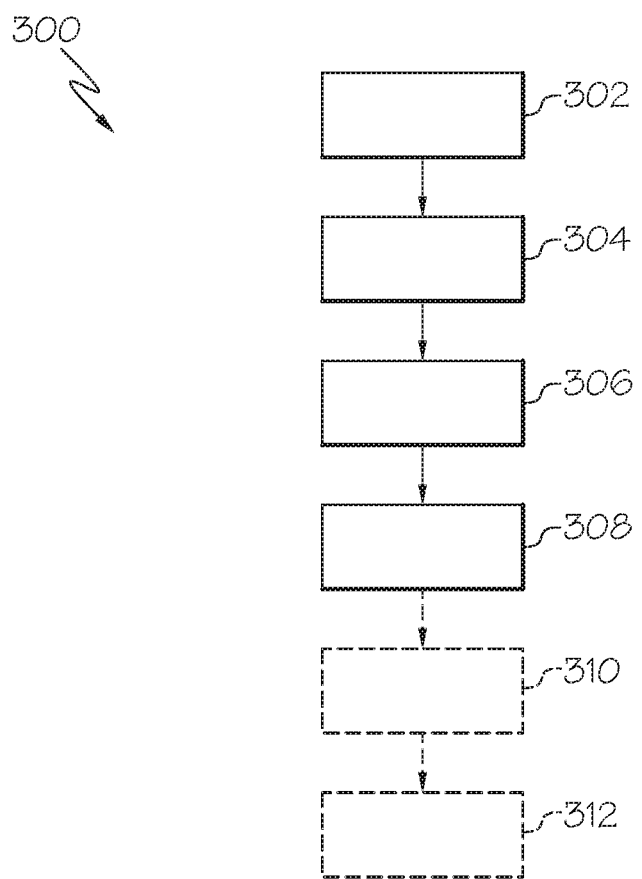
FIG. 3 depicts a flow chart illustrating a method for disabling a step-counting function of a wearable fitness tracker, according to one or more embodiments shown and described herein.

FIG. 3 illustrates flowchart depicting a method 300 for disabling the step-counting function of a wearable fitness tracker. At step 302, the method includes detecting a vehicle start-up event of the vehicle 10 with the one or more vehicle sensors 110, such as described herein. For example, the one or more vehicle sensors 110 may detect a door opening/closing, a person sitting on a seat, the ignition being activated, or any other event indicative of a vehicle start-up event.

At step 304, the method 300 includes sending an in-vehicle confirmation signal from the one or more vehicle communication modules 108 to the one or more wearable fitness trackers 200 positioned with the vehicle 10 in response to detecting the vehicle start-up event. For example, an audio signal, Bluetooth signal, radio frequency (RF) signal, cellular signal, or other wireless signal may be emitted by the one or more vehicle communication modules 108. At step 306, the one or more wearable fitness trackers 200 receive the in-vehicle confirmation signal. At step 308, upon receiving the in-vehicle confirmation signal, the one or more wearable fitness trackers may be caused to automatically disable at least the step-counting function of the one or more wearable fitness trackers based on the in-vehicle confirmation signal. For example, the one or more wearable fitness trackers 200 may include processors that are configured to process the signal and execute logic to cause the one or more wearable fitness trackers 200 to disable the step-counting function of the one or more wearable fitness trackers 200.

In some embodiments, the method 300 may further include, at step 310, detecting a vehicle-exiting event with the one or more vehicle sensors 110 such as described herein. For example, the one or more vehicle sensors 110 may detect a door opening/closing, a person leaving a seat, the vehicle stopping, the ignition being de-activated, or any other event indicative of a vehicle-exiting event. The method 300 may further include, at step 312, sending an out-of-vehicle confirmation signal from the one or more vehicle communication modules 108 to the one or more wearable fitness trackers 200 in response to detecting the exiting event. Sending the out-of-vehicle confirmation signal may cause the one or more wearable fitness trackers 200 to re-activate their step-counting (or other) functionality.

It should now be understood that embodiments disclosed herein are directed to systems and methods for disabling a step-counting function of a wearable fitness tracker while the wearable fitness tracker is positioned within a vehicle. A system generally includes one or more processors, one or more vehicle sensors, a one or more vehicle communication modules, and one or more memory modules. The system can detect a vehicle start-up event based on a vehicle start-up signal from the one or more vehicle sensors and second an in-vehicle confirmation signal from the one or more vehicle communication modules to the one or more wearable fitness trackers positioned within the vehicle in response to detecting the vehicle start-up event. The in-vehicle confirmation signal is configured to be received by the one or more wearable fitness trackers and cause the one or more wearable fitness trackers to automatically disable the step-counting function of the one or more wearable fitness trackers. Accordingly, false step counts that may occur when a user of a wearable fitness tracker is positioned within a vehicle (and not walking) may be avoided. Additionally, such systems may be able to communicate with the one or more wearable fitness trackers within needing to directly pair or connect the one or more wearable fitness trackers to the system or to the vehicle.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A method for disabling a step-counting function of a wearable fitness tracker, the method comprising:
   detecting a vehicle start-up event of a vehicle with one or more vehicle sensors; and
   sending an in-vehicle confirmation signal comprising an audio tone comprising a frequency outside of a range of about 20 HZ to about 20 kHz from one or more vehicle communication modules to one or more wearable fitness trackers positioned within the vehicle in response to detecting the vehicle start-up event;
   wherein the in-vehicle confirmation signal is configured to be received by the one or more wearable fitness trackers and cause the one or more wearable fitness trackers to automatically disable the step-counting function of the one or more wearable fitness trackers.

2. The method of claim 1, wherein the in-vehicle confirmation signal further comprises at least one of a radio frequency signal and a Bluetooth signal.

3. The method of claim 1, further comprising:
   detecting an vehicle-exiting event with the one or more vehicle sensors; and
   sending an out-of-vehicle confirmation signal from the one or more vehicle communication modules to the one or more wearable fitness trackers in response to detecting the vehicle-exiting event.

4. The method of claim 3, wherein:
   the in-vehicle confirmation signal is emitted by the one or more vehicle communication modules for a first time period of about 5 seconds or more upon detection the vehicle start-up event; and
   the out-of-vehicle confirmation signal is emitted by the one or more vehicle communication modules for a second time period upon detecting the vehicle-exiting event.

5. A system for disabling a step-counting function of a wearable fitness tracker, the system comprising:
   one or more processors;
   one or more vehicle sensors configured to output a vehicle start-up signal indicative of a vehicle start-up event of a vehicle;
   one or more vehicle communication modules communicatively coupled to the one or more processors and configured to output an in-vehicle confirmation signal comprising an audio tone comprising a frequency outside of a range of about 20 HZ to about 20 kHz; and
   one or more memory modules communicatively coupled to the one or more processors and storing logic, when executed by the one or more processors, causes the system to:
      detect the vehicle start-up event based on the vehicle start-up signal from the one or more vehicle sensors; and
      send the in-vehicle confirmation signal from the one or more vehicle communication modules to one or more wearable fitness trackers positioned within the vehicle in response to detecting the vehicle start-up event,
   wherein the in-vehicle confirmation signal is configured to disable the step-counting function of the one or more wearable fitness trackers in response to receiving the in-vehicle confirmation signal from the one or more vehicle communication modules.

6. The system of claim 5, wherein the in-vehicle confirmation signal further comprises at least one of a radio frequency signal and a Bluetooth signal.

7. The system of claim 5, wherein the logic executed by the one or more processors causes the system to:
   detect a vehicle-exiting event with based on a vehicle-exiting signal from the one or more vehicle sensors; and
   send an out-of-vehicle confirmation signal from the one or more vehicle communication modules to the one or more wearable fitness trackers in response to detecting the vehicle-exiting event.

8. The system of claim 7, wherein:
   the in-vehicle confirmation signal is emitted by the one or more vehicle communication modules for a first time period of about 5 seconds or more upon detection the vehicle start-up event; and
   the out-of-vehicle confirmation signal is emitted by the one or more vehicle communication modules for a second time period upon detecting the vehicle-exiting event.

* * * * *

UNITED STATES PATENT AND TRADEMARK OFFICE
CERTIFICATE OF CORRECTION

| | | |
|---|---|---|
| PATENT NO. | : 11,006,859 B2 | Page 1 of 1 |
| APPLICATION NO. | : 16/528969 | |
| DATED | : May 18, 2021 | |
| INVENTOR(S) | : Evan Vijithakumara | |

It is certified that error appears in the above-identified patent and that said Letters Patent is hereby corrected as shown below:

On the Title Page

Column 2, item (56), U.S. Patent Documents, cite no. 8, delete "Rajendran" and insert --Rajendran et al.--, therefor.

In Page 2, Column 1, item (56), U.S. Patent Documents, cite no. 10, delete "Tu" and insert --Tu et al.--, therefor.

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*